United States Patent
Anton et al.

(10) Patent No.: US 6,525,231 B1
(45) Date of Patent: Feb. 25, 2003

(54) PRODUCING HYDROFLUORO COMPOUNDS BY HYDROGENOLYSIS OF IODIDES

(75) Inventors: Douglas Robert Anton, Claymont, DE (US); Carl George Krespan, Wilmington, DE (US); Allen Capron Sievert, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 08/043,917

(22) Filed: Apr. 7, 1993

Related U.S. Application Data

(63) Continuation-in-part of application No. 07/964,973, filed on Oct. 22, 1992, now abandoned.

(51) Int. Cl.$^7$ .............................................. C06T 21/22
(52) U.S. Cl. ..................................................... 570/176
(58) Field of Search ........................................ 570/176

(56) References Cited

U.S. PATENT DOCUMENTS

| | | | |
|---|---|---|---|
| 2,844,636 A | | 7/1958 | Haszeldine et al. |
| 2,942,036 A | | 6/1960 | Smith et al. |
| 3,042,727 A | * | 7/1962 | Olstowski et al. .......... 570/176 |
| 3,132,185 A | | 5/1964 | Parsons |
| 4,243,770 A | | 1/1981 | Tatemoto et al. |
| 4,275,226 A | | 6/1981 | Yamabe et al. |
| 5,097,082 A | | 3/1992 | Anton |
| 5,648,568 A | | 7/1997 | Oharu et al. .......... 570/176 |

FOREIGN PATENT DOCUMENTS

| | | |
|---|---|---|
| GB | 1578933 | 5/1977 |

OTHER PUBLICATIONS

Haszeldine, J. Chem. Soc., pp. 3761–3768 (1953).*
R. W. Haszeldine, *J. Chem. Soc.*, pp. 3761–3768 (1953).
Houben–Weyl, *Methoden Der Organische Chemie* Band 4:653–655 (1960).
C. G. Krespan, *J. Org. Chem.* 23:2016:2017 (1958).
R. W. Haszeldine et al., "Fluor–olefins. Part III", Univ. Chem. Lab. Cambridge, pp. 3880–3888.
Bekker et al., *IZV. Akad. Nauk SSSR, Ser. Khim.*, pp. 2738–2741 (1970).
Gard and Wolf. *J. Fluorine Chem.*, 1:487–492 (1971/2).
Hutchinson, *J. Fluorine Chem.*, 3:429–432 (1973/4).
Tortelli et al., *J. Flourine Chem.*, 47:199–217 (1990).
Chem. Abst. 111(24):216717x.

* cited by examiner

*Primary Examiner*—Johann Richter
*Assistant Examiner*—Elvis O. Price

(57) ABSTRACT

A process is disclosed for producing RCFZH by reaction of an iodide compound of the formula R'CFZI with hydrogen at an elevated temperature, wherein R is $SF_5$, $CF_2SF_5$ or $R_fCF_2Y$, R' is $SF_5$, $CF_2SF_5$ or $R_fCF_2X$, $R_f$ is a perfluoroalkylene group containing from 1 to about 12 carbon atoms and optionally containing one or more ether oxygen atoms, Z is selected from F, $CF_3$ and $CF_2CF_3$, Y is selected from H, F and $SF_5$, and X is selected from H, F, $SF_5$, and I, provided that when Y is F, X is F, when Y is $SF_5$, X is $SF_5$, and when Y is H, X is H or I.

16 Claims, No Drawings

PRODUCING HYDROFLUORO COMPOUNDS BY HYDROGENOLYSIS OF IODIDES

This application is a continuation-in-part of U.S. patent application Ser. No. 07/964,973, filed Oct. 22, 1992 which is now abandoned.

FIELD OF THE INVENTION

This invention relates to the production of compounds containing fluorine-substituted carbon atoms, and more particularly to the production of hydrofluoro compounds containing multiple carbon atoms and/or both carbon and sulfur atoms.

BACKGROUND OF THE INVENTION

Multicarbon compounds and carbon-sulfur compounds which contain hydrogen and fluorine but no chlorine, have recently been the subject of renewed interest as environmentally desirable compounds for use as solvents, blowing agents and refrigerants. Among these compounds are certain hydrofluorocarbons (i.e., compounds containing only carbon, hydrogen and fluorine) which have typically been produced using catalytic processes for hydrogenolysis and/or hydrogenation of saturated or unsaturated compounds containing both chlorine and fluorine. Certain supported precious metal catalysts are among those considered particularly suited for catalyzing the reactions. British Patent Specification No. 1,578,933 uses a process for the manufacture of $CF_3CH_2F$ or $CHF_2CHF_2$ by the hydrogenolysis of an appropriate haloethane (e.g., $CF_3CCl_2F$) over a hydrogenation catalyst such as palladium supported on carbon or alumina. Conventional hydrogenolysis of this type can be used to convert $CF_3CCl_2F$ to a product mixture including $CF_3CHClF$ and $CF_3CH_3$ in addition to tetrafluoroethane.

Precious metal catalysts such as palladium are expensive and can deactivate during the course of catalyzed reactions. Replacement and/or regeneration of such catalysts can thus add to the cost of the catalyzed reaction. Also, the use of chlorine-containing reactants such as $CF_3CCl_2F$ and the production of chlorine-containing products such as $CF_3CHClF$ can present handling and disposal concerns.

Iodine or hydrogen iodide have been used in conjunction with the reaction of selected fluorine-containing compounds. For example, U.S. Pat. No. 2,844,636 discloses a process for the manufacture of 1,1,2,3,4,4-hexafluorobutane by reacting perfluoro-cyclobutene with hydrogen, using elemental iodine as a catalyst. In this process not only is there hydrogen addition at the double bond, but also cleavage and hydrogenation at the $—CF_2—CF_2—$ single bond to give the substituted normal butane. U.S. Pat. No. 5,097,082 discloses a process for producing saturated halohydro-carbons containing fluorine which comprises the step of reacting certain saturated or olefinic compounds at an elevated temperature with hydrogen in the presence of at least one material selected from the group consisting of iodine and hydrogen iodide, or with hydrogen iodide.

SUMMARY OF THE INVENTION

A process is provided in accordance with this invention for producing a compound of the formula RCFZH wherein R is selected from the group consisting of $SF_5$, $CF_2SF_5$ and $R_fCF_2Y$, $R_f$ is a perfluoroalkylene group containing from 1 to about 12 carbon atoms and optionally containing one or more ether oxygen atoms, Y is selected from H, F, and $SF_5$ and Z is selected from $CF_2CF_3$, $CF_3$ and F, by reaction of an iodide compound of the formula R'CFZI with hydrogen at an elevated temperature, wherein wherein R' is selected from the group consisting of $SF_5$, $CF2SF_5$ and $R_fCF_2X$ and X is selected from H, F, $SF_5$, and I, provided that when Y is F, X is F, when Y is $SF_5$, X is $SF_5$ and when Y is H, X is H or I.

DETAILS OF THE INVENTION

This invention provides a process for producing monohydro and dihydro compounds from corresponding monoiodo and diiodo compounds. The monoiodo and diiodo reactants of this invention include compounds with multiple adjacent carbons (i.e., C—C bonds) and/or carbon adjacent to sulfur (i.e., C—S bonds). The monoiodo and diiodo reactants are reacted in accordance this invention essentially without cleavage of these carbon-carbon and carbon-sulfur bonds. The iodide compound reactants of this invention contain an iodine which is either on a difluoro-substituted carbon (i.e., Z is F) or on a monofluoro-substituted carbon adjacent to a $CF_3$ or $C_2F_5$ group (i.e., Z is $CF_3$ or $CF_2CF_3$). The diiodo compounds all contain at least one iodine which is on a difluoro-substituted carbon. Preferably Z is F, especially when R' is $R_fCF_2X$.

The monoiodo and diiodo compounds which are reacted in accordance with this invention include (where R' is $R_fCF_2X$ and X is H, F or I) any perfluoroalkyl iodide, perfluoroalkyl diiodide or ω-H-perfluoroalkyl iodide containing from 3 to about 14 carbon atoms and optionally containing one or more ether oxygen atoms. The perfluoroalkylene group, $R_f$, may be branched or unbranched. Examples of perfluoroalkyl groups which do not contain ether oxygens include for example, $—CF_2—$, $—CF_2CF_2—$, $—CF_2C(CF_3)F—$, $—CF_2CF_2CF_2—$, $—CF_2C(CF_3)_2—$ and $—CF_2CF_2CF_2CF_2—$. Examples of perfluoroalkylene groups which contain ether oxygens include for example, $—CF_2OCF_2—$, $—CF_2CF_2OCF_2—$, $—CF_2OCF_2OCF_2—$, $—CF_2OCF_2CF_2OCF_2—$, $—CF_2CF_2OCF(CF_3)CF_2OCF_2—$, and $—CF_2OCF_2CF(CF_3)OCF_2CF_2OCF(CF_3)CF_2OCF_2—$.

Preferred iodides include mono- and diiodides of the structures $CF_3R_fCF_2I$ and $ICF_2R_fCF_2I$, where $R_f$ is $C_1$ to $C_{10}$ perfluoroalkylene, branched or unbranched, and optionally containing one or more ether linkages. Most preferred are iodides of the linear structures $F(CF_2)_nI$ and $I(CF_2)_nI$ where n is an integer from 3 to 12. Examples include $I(CF_2)_4I$, $I(CF_2)_6I$, $F(CF_2)_4I$, $F(CF_2)_6I$, and $F(CF_2)_8I$.

Perfluoroalkyl iodides may be prepared by the addition of either trifluoroiodomethane or pentafluoroiodoethane to tetrafluoroethylene as disclosed by R. N. Haszeldine, J. Chem. Soc., pp. 3761–3768 (1953). Perfluoroalkyl diiodides containing an even number of carbon atoms may be prepared by the addition of 1,2-diodoperfluoroethane to tetrafluoroethylene as disclosed in Houben-Weyl, "Methoden Der Organische Chemie" Band V/4, pp. 653–655 (1960). In a similar manner perfluoroalkyl diiodides containing an odd number of carbon atoms may be prepared by the addition of 1,3-diodoperfluoropropane to tetrafluoroethylene. ω-H-perfluoroalkyl iodides may be prepared by the reaction of an ω-H-perfluoroalkyl acid chloride with potassium iodide as disclosed by C. G. Krespan, J. Org. Chem., Vol. 23, pp. 2016–2017 (1958). Perfluoroalkyl iodides containing $C_3$ to $C_{14}$ carbon atoms and optionally containing one or more ether oxygens may be prepared as disclosed in U.S. Pat. No. 4,275,226, which is hereby incorporated herein in its entirety by reference (see in particular col. 2, lines 46–65).

The monoiodo compounds which are reacted in accordance with this invention also include carbon-sulfur compounds having a pentafluoro sulfur group. Examples include $SF_5CF_2I$ and $SF_5CFICF_3$ (i.e., R' is $SF_5$) and $SF_5CF_2CF_2I$ (i.e., R' is $CF_2SF_5$ and Z is F). $SF_5CF_2I$ has been prepared by reaction of the silver salt of $SF_5CF_2CO_2H$ with iodine as disclosed by Bekker, et al. in IZV. Akad. Nauk SSSR, Ser. Khim., pp. 2738–2741 (1970). $SF_5CFICF_3$ has been prepared by reaction of $SF_5CF=CF_2$ with a mixture of iodine and $IF_5$ as reported by Gard and Woolf in J. Fluorine Chem., Vol. 1, pp. 487–492 (1971/2). Longer chain $SF_5$-terminated reactants can generally be prepared in a manner analogous to $CF_3$-terminated compounds. $SF_5$-substituted iodofluoroalkanes containing an even number of carbon atoms ($SF_5(CF_2CF_2)_nI$, where n is an integer from 1 to about 6) may be prepared by reacting $S_2F_{10}$ with $CF_2ICF_2I$ or with $I_2$ and tetrafluoroethylene as disclosed by Hutchinson in J. Fluorine Chem., Vol. 3, pp. 429–432 (1973/4).

The hydrogenolysis reaction of this invention may advantageously be accomplished in the absence of hydrogenation catalysts. The term "hydrogenation catalysts" is used herein in the ordinary sense, to signify conventional metal-based hydrogenation catalysts which are in themselves known. Examples of hydrogenation catalysts include nickel or other metals of Group VIII of the Periodic Table (in catalytic form) or oxides or salts thereof. (In use, a compound of such a metal is reduced at least in part to the metal.) In particular, the reaction of this invention may be accomplished in the absence of palladium hydrogenation catalysts. Preferably, the reaction is accomplished in the absence of any supported metal catalysts.

Substantial amounts of iodine are generally produced during the reaction. The iodine recovered from the reaction of hydrogen with the additional monoiodoperfluoroalkanes or diiodoperfluoroalkanes may be recycled by using it to prepare monoiodoperfluoroalkanes or diiodoperfluoroalkanes (e.g., by reacting it with tetrafluoroethylene). $\alpha,\omega$-diiodoperfluoroalkanes may be prepared by the reaction of tetrafluoroethylene with iodine as disclosed by Tortelli et al., J. Fluorine Chem., Vol. 47, pp. 199–217 (1990). Monoiodoperfluoroalkanes may be prepared by reaction of tetrafluoroethylene with iodine in the presence of $IF_5$ and $SbF_5$ as disclosed in U.S. Pat. No. 3,132,185. The iodine produced during the hydrogenolysis may also be used to form potassium iodide. The conversion of iodine to potassium iodide is a well known reaction (see, e.g., CA 111 (24): 216717x). The potassium iodide can then be used to prepare additional amounts of the various mono- and diiodine reactants (i.e., additional iodide compound reactants). For example, KI may be reacted with a $\omega$-H-perfluoroalkyl acid chloride as indicated above to provide a $\omega$-H-perfluoroalkyl iodide.

Substantial amounts of HI may be produced, particularly where excess hydrogen is used during the reaction. The HI can also be used to make $I_2$ (by oxidation) or KI (by neutralization).

Free iodine may be added to the reaction, and may be useful to moderate exothermic reactions at the start of the hydrogenolysis. However, the presence of free iodine is not considered essential for the hydrogenolysis and the reaction may be accomplished without addition of supplemental iodine.

The reaction is performed at an elevated temperature. The reaction temperature should generally be from about 200° C. to about 500° C. The temperature is preferably about 400° C. or less to minimize corrosion, energy requirements, and side reactions (e.g., carbon-carbon bond cleavage). A preferred range is 250° C. to 350° C. Hydrogenation of diiodo compounds at lower temperatures (e.g., about 200–225° C.) typically results in formation of significant amounts of monoiodo compound, which can then be further hydrogenated (by recycle or otherwise) to form the desired dihydro compound.

Typically, the ratio of hydrogen to the iodide compound reactant is within the range of about 10:1 to 1:10. It is preferred that hydrogen be present in no more than stoichiometric amounts. The mole ratio of hydrogen (i.e., $H_2$) to monoiodo compounds is preferably from about 1:2 to about 1:4, and is more preferably about one mole of hydrogen for each two moles of such compounds. The mole ratio of hydrogen to diiodo compounds is preferably from about 1:1 to about 1:2, and is more preferably about 1:1. The hydrogen can be fed either in the pure state or diluted with an inert gas, e.g., nitrogen, helium, or argon. A particular advantage of using no excess hydrogen is that essentially all of the hydrogen may be used for hydrogenolysis; and that there is consequently an absence or near absence of hydrogen and hydrogen iodide in the resulting product. This facilitates the isolation and purification of the hydrogenolysis product. Iodide compounds remaining in the product mixture may be recycled.

The reaction may be operated either in a batch or continuous mode at pressures of from about 10 kPa to about $20 \times 10^3$ kPa with 101 kPa to about $7 \times 10^3$ kPa being preferred.

The products of the reaction can be separated and purified by conventional means such as fractional distillation. The products are useful as stable, nonflammable solvents (see, e.g., U.S. Pat. No. 4,243,770), refrigerants, propellants, and cleaning and drying agents.

Practice of the invention will become further apparent from the following non-limiting examples.

EXAMPLE 1

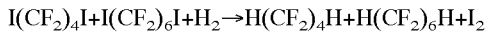

A 225-mL Hastelloy™ nickel alloy tube was charged with 90.8 g (0.20 mol, 36 mL) of 1,4-diiodoperfluorobutane which contained 2.4 wt % of 1,6-diiodoperfluorohexane and 0.5 g (0.002 mol) of iodine. The tube was then cooled to −80°C., evacuated, warmed to 22° C., and pressured to 412 psi (2.94 mPa) with hydrogen (0.22 mol). During heating at 250° C. for 3 hours, a pressure drop from 818 psi (5.74 mPa) to 789 psi (5.54 mPa) was observed. The temperature was raised to 300° C., where the pressure fell rapidly from 895 psi (6.27 mPa) and leveled at 639 psi (4.51 mPa) over a 2 hour period.

The reactor, when cooled to 25° C., showed a pressure of 30 psi (3.0 kPa) and contained solid iodine along with 36.0 g of liquid. GC analysis showed the product to be 96.9% 1H,4H-perfluorobutane and 2.3% 1H,6H-perfluorohexane, with 0.8% of a higher boiler present. $^1H$ and $^{19}F$ NMR analyses confirmed the structure assignments. Yields were 35.2 g (88%) of $H(CF_2)_4H$ and 0.8 g (70%) of $H(CF_2)_6H$ with iodine as substantially the only other product.

EXAMPLE 2

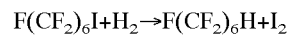

A 225-mL Hastelloy™ nickel alloy tube was charged with 134.0 g (0.30 mol) of perfluorohexyl iodide, cooled to −80° C. and evacuated, then warmed to 22° C. and pressured to 380 psi (2.72 mPa) with hydrogen (0.17 mol). Heating to 300° C. was accompanied by at least three temperature spikes, the first beginning at 240° C. The pressure at 300° C. began at 990 psi (6.93 mPa) and dropped to 860 psi (6.03 mPa) within 2 hours. When cooled to 25° C., the reactor showed zero pressure on the gauge. Distillation of the liquid product afforded 77.9 g (81%) of pure 1H-perfluorohexane (Boiling Point 70.6–71.2° C.), confirmed by GC and NMR.

EXAMPLE 3

$I(CF_2)_4I + I(CF_2)_6I + H_2 \rightarrow H(CF_2)_4H + H(CF_2)_6H + I_2$

The reaction of Example 1 was repeated without added iodine and with a time at 300° C. of 2 hours. Pressure behavior showed reaction to be essentially complete in 20 minutes. The product was shown by GC to be an 88% yield of 1H,4H-perfluorobutane and a 91% yield of 1H,6H-perfluorohexane.

EXAMPLE 4

$I(CF_2)_4I + H_2 \rightarrow H(CF_2)_4H + I_2$

The reaction of Example 3 was repeated in a 240 mL Hastelloy™ nickel alloy tube with water-white $I(CF_2)_4I$ obtained by shaking with mercury just before addition to the tube. The tube was then cooled to −80° C., evacuated, warmed to 22.6° C., and pressured to 303 psi (2.13 mPa) with hydrogen (0.17 mol). Pressure at 300° C. fell from 821 psi (5.76 mPa) to about 625 psi (4.39 mPa) in 30 min. and remained there for 30 more minutes. Decantation at about −20° C. from free iodine gave 34.5 g of liquid that was shown by GC to contain 23.5 g (60% conv.) of $H(CF_2)_4H$, 0.7 g of $H(CF_2)_6H$, 8.7 g (15% conv.) of $I(CF_2)_4H$, 0.2 g of $I(CF_2)_6H$ and 1.3 g (1% recovery) of $I(CF_2)_4I$.

This example illustrates the thermal reduction process using a 15% deficiency of hydrogen.

EXAMPLE 5

$I(CF_2)_4I + H_2 \rightarrow H(CF_2)_4H + I_2$

A 400 mL Hastelloy™ nickel alloy reaction bomb was charged with $I(CF_2)_4I$ (50.0 g, 0.11 mole) and two crystals of iodine. The bomb was purged with nitrogen three time, placed in an autoclave, agitated, pressurized with 100 psig (791 kPa) of hydrogen. The bomb was then warmed to 200° C. and the total pressure of the system brought to 500 psig (3548 kPa) with additional hydrogen. The bomb was held at 215–220° C. for 12 hours, cooled, and the contents discharged. The product, weighing 38.3 g, consisted of a purple supernatant over crystalline iodine. GC analysis of the supernatant indicated the following composition:

| Component | GC Area % |
|---|---|
| $H(CF_2)_4H$ | 8.8 |
| $H(CF_2)_4I$ | 50.1 |
| $I(CF_2)_4I$ | 40.8 | along with traces (<0.1%) of $H(CF_2)_6I$ and $I(CF_2)_6I$ and several other unidentified products.

EXAMPLE 6

$I(CF_2)_4I + H_2 \rightarrow H(CF_2)_4H + I_2$

Following a procedure similar to that of Example 5, a 400 mL Hastelloy™ nickel alloy reaction bomb was charged with $I(CF_2)_4I$ (50.0 g, 0.11 mole). After purging with nitrogen, the bomb was charged with 30 psig (308 kPa) of hydrogen at a temperature of −43° C. (0.064 mole by the ideal gas law). The bomb was then warmed to 214–220° C. for 12 hours, cooled, and the contents discharged. The product, weighing 42.4 g, consisting of a purple supernatant over crystalline iodine. GC analysis of the supernatant indicated the following composition:

| Component | GC Area % |
|---|---|
| $H(CH_2)_4H$ | 0.25 |
| $H(CF_2)_4I$ | 13.4 |
| $I(CF_2)_4I$ | 85.9 | along with traces (<0.2%) of $H(CF_2)_6I$, $I(CF_2)_6I$, $I(CF_2)_3I$, and several other unidentified products.

EXAMPLE 7

$F(CF_2)_6I + H_2 \rightarrow C_6F_{13}H + I_2$

A 400 mL Hastelloy™ nickel alloy reaction bomb was charged with $C_6F_{13}I$ (100 g, 0.22 mole). The bomb was cooled, evacuated and pressurized with 1500 psig (10.4×10³ kPa) of hydrogen. The bomb was then warmed to 200° C. for one hour, 240° C. for one hour and 250° C. for ten hours. The bomb was then cooled, vented, and the contents discharged. GC analysis showed the liquid to be 99% $C_6F_{13}H$ and 1% $C_6F_{13}I$.

It is understood that the invention is not confined to the particular formulations and examples herein illustrated, but it embraces such modified forms thereof as come within the scope of claims which follow.

What is claimed is:

1. A process for producing a compound of the formula RCFZH wherein R is selected from the group consisting of $SF_5$, $CF_2SF_5$ and $R_fCF_2Y$, wherein $R_f$ is a perfluoroalkylene group containing from 1 to about 12 carbon atoms and optionally containing one or more ether oxygen atoms, Y is selected from the group consisting of H, F and $SF_5$, and Z is selected from the group consisting of F, $CF_3$ and $CF_2CF_3$ comprising: reacting an iodide compound of the formula R'CFZI with hydrogen at an elevated temperature of about 400° C. or less in the absence of metal-based hydrogenation catalysts, wherein R' is selected from the group consisting of $SF_5$, $CF_2SF_5$ and $R_fCF_2X$ and wherein X is selected from the group consisting of H, F and $SF_5$ and I, provided that when Y is F, X is F, when Y is $SF_5$, X is $SF_5$ and when Y is H, X is H or I.

2. The process of claim 1 wherein the reaction temperature is from about 200° C. to about 400° C.

3. The process of claim 2 wherein said reaction temperature is from about 200° C. to 350° C.

4. The process of claim 2 wherein said reaction temperature is from about 250° C. to 400° C.

5. The process of claim 2 wherein the iodide compound is a monoiodo compound, and wherein the mole ratio of hydrogen to the iodide compound is from about 1:2 to about 1:4.

6. The process of claim 2, claim 3, claim 4, or claim 5 wherein an iodide compound selected from the group consisting of $SF_5CF_2I$, $SF_5CFICF_3$ and $SF_5CF_2CF_2I$ is reacted with hydrogen.

7. The process of claim 2, claim 3, claim 4, or claim 5 wherein the iodide compound has the formula $CF_3R_fCF_2I$; and wherein $R_f$ is $C_1$ to $C_{10}$ perfluoroalkylene, branched or unbranched, and optionally containing one or more ether linkages.

8. The process of claim 2, claim 3, claim 4, or claim 5 wherein the iodide compound has the linear structure $F(CF_2)_nI$ wherein n is an integer from 3 to 12.

9. The process of claim 2 wherein the iodide compound is a diiodo compound, and wherein the mole ratio of hydrogen to the iodide compound is from about 1:1 to about 1:2.

10. The process of claim 2, claim 3, claim 4, or claim 9 wherein the iodide compound has the formula $ICF_2R_fCF_2I$, and wherein $R_f$ is $C_1$ to $C_{10}$ perfluoroalkylene, branched or unbranched, and optionally containing one or more ether linkages.

11. The process of claim 2, claim 3, claim 4, or claim 9 wherein the iodide compound has the linear structure $I(CF_2)_nI$ wherein n is an integer from 3 to 12.

12. The process of claim 2 wherein iodine produced by the reaction is used to form potassium iodide; and wherein said potassium iodide is used to prepare additional iodide compound reactants.

13. The process of claim 2 wherein iodine produced by the reaction is recycled by reacting it with tetrafluoroethylene to prepare monoiodoperfluoroalkanes or diiodoperfluoroalkanes.

14. The process of claim 2 wherein the iodide compound is selected from the group consisting of $I(CF_2)_4I$, $I(CF_2)_6I$, $F(CF_2)_4I$, $F(CF_2)_6I$, and $F(CF_2)_8I$.

15. The process of claim 1 wherein the diiodo compound is reacted at about 200 to 225° C. to form significant amounts of a monoiodo compound; and wherein the monoiodo compound formed is further hydrogenated to form a dihydro compound.

16. The process of claim 1 wherein the reaction temperature is from about 250° C. to 350° C.

* * * * *